(12) United States Patent
von Aspern et al.

(10) Patent No.: US 10,722,439 B2
(45) Date of Patent: Jul. 28, 2020

(54) HAIR CARE PRODUCTS

(71) Applicant: Henkel AG & Co. KGaA, Duesseldorf (DE)

(72) Inventors: Edith von Aspern, Harnstedt (FR);
Dirk Hentrich, Hamburg (DE);
Manuela Mette, Kleinfeld (DE);
Thomas Schroeder, Hamburg (DE);
Soeren Scheele, Pinneberg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/021,865

(22) Filed: Jun. 28, 2018

(65) Prior Publication Data

US 2019/0021968 A1    Jan. 24, 2019

(30) Foreign Application Priority Data

Jul. 19, 2017   (DE) .................. 10 2017 212 403

(51) Int. Cl.
   *A61K 8/42*   (2006.01)
   *A61Q 5/12*   (2006.01)
   *A61K 8/31*   (2006.01)
   *A61K 8/37*   (2006.01)
   *A61K 8/41*   (2006.01)
   *A61Q 5/02*   (2006.01)

(52) U.S. Cl.
   CPC .............. *A61K 8/42* (2013.01); *A61K 8/31* (2013.01); *A61K 8/37* (2013.01); *A61K 8/416* (2013.01); *A61Q 5/12* (2013.01); *A61K 2800/34* (2013.01); *A61K 2800/5426* (2013.01); *A61Q 5/02* (2013.01)

(58) Field of Classification Search
   None
   See application file for complete search history.

(56) References Cited

U.S. PATENT DOCUMENTS

| | | | | |
|---|---|---|---|---|
| 6,274,128 B1 * | 8/2001 | Bergmann | ............... | A61K 8/19 |
| | | | | 424/400 |
| 8,956,598 B2 * | 2/2015 | Jackwerth | ............... | A61K 8/31 |
| | | | | 424/65 |
| 9,095,528 B2 * | 8/2015 | Desenne | .................. | A61K 8/31 |
| 2008/0287722 A1 | 11/2008 | Dierker | | |
| 2016/0326091 A1 | 11/2016 | Rudolph et al. | | |

FOREIGN PATENT DOCUMENTS

| | | | | |
|---|---|---|---|---|
| CN | 107648073 A | 2/2018 | | |
| WO | 2010115973 A1 | 10/2010 | | |
| WO | WO-2010115973 A1 * | 10/2010 | ............... | A61K 8/31 |

OTHER PUBLICATIONS

Lohninger, Hans; List of Alkanes, accessed May 20, 2019 (Year: 2019).*
Schaefer (Conditioning Agents for Hair Formulations, Oct. 30, 2008). (Year: 2008).*
De la lastra products (website www.delalastra.com, available online Mar. 15, 2017 (Year: 2017).*
De la lastra products use of (website www.delalastra.com, available online Mar. 15, 2017 (Year: 2017).*
Lohninger, Hans; List of Alkanes, see attached, accessed May 20, 2019 (Year: 2019).*
De la Lastra products and methods of use (website www.delalastra.com, available online Mar. 15, 2017 (Year: 2017).*

* cited by examiner

*Primary Examiner* — Robert A Wax
*Assistant Examiner* — Melissa S Mercier
(74) *Attorney, Agent, or Firm* — Lorenz & Kopf, LLP

(57) ABSTRACT

Hair treatment agents containing a mixture of special linear alkanes, an amidoamine and/or a cationized amidoamine, and at least one cationic surfactant (esterquat and/or quaternary ammonium compound) are provided. In one example, the hair treatment agents are suitable for the care of hair, in particular to improve the wet and dry combability, the disentanglement, the hold, and the gloss of hair.

13 Claims, No Drawings

HAIR CARE PRODUCTS

CROSS-REFERENCE TO RELATED APPLICATION

This application claims priority to German Patent Application No. 10 2017 212 403.2, filed Jul. 19, 2017, which is incorporated herein by reference in its entirety.

TECHNICAL FIELD

The application describes hair treatment agents based on an active ingredient combination of specific linear alkanes and cationic and cationizable nourishing agents, a method for treating hair with these agents, and the use of these agents to nourish keratinous fibers.

BACKGROUND

Besides natural environmental influences, human hair is also exposed to a series of other, particularly cosmetic, stresses. These hair-straining stresses include, for example, the coloring of hair and its deformation, for example by perming. Cosmetic hair care products are used to reduce the negative effects of the (environmental) influences impairing the hair structure, while also retaining and improving the natural hair structure. Silicon-organic compounds are an essential active ingredient in many of these cosmetic agents, in particular silicons such as trisiloxane, which are exemplified by nurturing properties. The disadvantages of these silicons are the reduced penetration of active and auxiliary ingredients into the hair and the complication of hair styling, each caused by the moistening of the hair surface. Furthermore, for reasons of sustainability, efforts must be made to use as high a proportion of bio-degradable active ingredients as possible in cosmetic products. The preparation of low-silicon or silicon-free care products is therefore a relevant problem in the field of hair cosmetics.

In the prior art, the group of linear paraffins was discussed as one of numerous active ingredient classes suitable for the substitution of the silicons. For example, the patent application WO 2010/115973A1 (Biosynthis) describes cosmetic compositions that contain mixtures of linear $C_8$-$C_{12}$ alkanes and $C_{14}$-$C_{24}$ alkanes in addition to other constituents. However, these compositions still have a range of disadvantages and, despite previous achievements, there is still a demand for low-silicon or silicon-free hair care products based on volatile light emollients.

BRIEF SUMMARY

Hair treatment agents are provided herein. In an exemplary embodiment, a hair treatment agent includes a) at least one linear alkane selected from C9-, C10-, C11- and C12 alkanes and mixtures of these alkanes, b) at least one linear alkane selected from C15-, C16-, C17-, C18-, C19-, C20-, C21-, C22- and C23 alkanes and mixtures of these alkanes, c) at least one amidoamine and/or a cationized amidoamine, and d) at least one cationic surfactant selected from esterquats and/or quaternary ammonium compounds.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has now been found that hair care products with an excellent nurturing effect can be obtained by combining specific linear alkanes with specific cationic and cationizable nourishing agents.

These agents with viscosity and storage stability give the treated hair good gloss properties, an improved hold, and excellent disentanglement and combability.

A first subject of this application is a hair treatment agent, containing
  a) at least one linear alkane selected from C9-, C10-, C11- and C12 alkanes and mixtures of these alkanes,
  b) at least one linear alkane selected from C15-, C16-, C17-, C18-, C19-, C20-, C21-, C22- and C23 alkanes and mixtures of these alkanes,
  c) at least one amidoamine and/or a cationized amidoamine, and
  d) at least one cationic surfactant selected from
    (i) esterquats and/or
    (ii) quaternary ammonium compounds.

Hair treatment agents in the context of the present disclosure are, for example, hair coloring agents, bleaching agents, hair shampoos, hair conditioners, conditioning shampoos, hair sprays, hair rinses, hair masks, hair packs, hair tonics, perm fixing solutions, hair dye shampoos, hair setting lotions, hair setting agents, hair styling preparations, blow-dry lotions, mousses, hair gels, hair waxes, and combinations thereof.

The hair treatment agents as contemplated herein are preferably hair conditioners, conditioning shampoos, hair rinses, hair masks, hair packs, or hair tonics.

Suitable cosmetic carriers are, in particular, O/W, W/O and W/O/W emulsions in the form of creams or gels, or surfactant-containing foaming solutions, such as shampoos, foaming aerosols, foam formulations or other preparations suitable for application on the hair. However, it is also conceivable that the ingredients could be integrated in a powdery or a tablet-like formulation, which is dissolved in water prior to application.

In a particularly preferred embodiment, the cosmetic carrier is hydrous or hydrous-alcoholic.

A hydrous cosmetic carrier preferably contains at least about 50 wt. % water.

In the context of the present disclosure, hydrous-alcoholic cosmetic carriers should be understood as hydrous solutions that, besides water, contain from about 3 to about 40 wt. % of one $C_1$-$C_6$ alcohol, in particular methanol, ethanol or propanol, isopropanol, butanol, isobutanol, tert-butanol, n-pentanol, iso-pentanol, n-hexanol, iso-hexanol, propylene glycol, glycol, glycerol, 1.2-pentanediol, 1.5-pentanediol, 1.2-hexanediol or 1.6-hexanediol. The agents as contemplated herein can also contain other organic solvents, such as methoxybutanol, benzyl alcohol, ethyldiglycol or 1.2-propylene glycol. All water-soluble organic solvents are preferred.

In a particularly preferred embodiment, the hair treatment agents as contemplated herein contain at least about 50 wt. % water and at least from about 0.1 to about 20 wt. %, preferably from about 0.1 to about 10 wt. %, more preferably from about 0.1 to about 5.0 wt. %, particularly preferably from about 0.1 to about 3.0 wt. %, and most preferably from about 0.1 to about 1.0 wt. % of one $C_1$-$C_6$ alcohol, in particular methanol, ethanol or propanol, isopropanol, butanol, isobutanol, tert-butanol, n-pentanol, iso-pentanol, n-hexanol, iso-hexanol, glycol, propylene glycol, glycerol, 1.2-pentanediol, 1.5-pentanediol, 1.2-hexanediol, or 1.6-hexanediol as the cosmetic carrier. In this embodiment, the $C_1$-$C_6$ alcohol is more preferably selected from ethanol, propylene glycol, glycerol, 1.2-pentanediol, 1.5-pentanediol, 1.2-hexanediol or 1.6-hexanediol. In this embodiment the $C_1$-$C_6$ alcohol is particularly preferably selected from propylene glycol and glycerol. Glycerol is most preferably used.

The hair treatment agents as contemplated herein contain a mixture of specific linear alkanes (a) and b)) as essential constituents.

This mixture of specific alkanes is exemplified by problem-free incorporation into hair care products with a high proportion of cationic and cationizable nourishing agents. The resulting hair care products can be distributed excellently in the hair and do not leave an oily, heavy feeling after rinsing. In comparison with silicones in corresponding hair treatment agents, they also have the surprising advantage that they cause an improved hair-nourishing effect—in particular improved sensory properties and combability properties.

As for the cosmetic effect, the use of linear alkanes a), containing at least about 50 wt. % $C_{12}$ alkane (dodecane), has proven particularly advantageous.

As for the cosmetic effect, the use of
linear alkanes b), containing at least about 50 wt. % $C_{22}$ alkane (docosane), has proven even more particularly advantageous.

As for the cosmetic effect, the use of linear alkanes a) known under the International Nomenclature Cosmetic Ingredient (INCI) name dodocane and linear alkanes b) known under the INCI name docosane has proven most advantageous.

In a first preferred embodiment, corresponding hair treatment agents are exemplified in that they contain at least about 50 wt. % $C_{12}$ alkane (dodecane) and at least about 50 wt. % $C_{22}$ alkane (docosane).

In a second preferred embodiment, the hair treatment agents as contemplated herein contain
 at least one linear alkane a) known under the INCI name Dodecane and
 at least one linear Alkane b) known under the INCI name Docosane.

The linear alkanes a) and b) are preferably available exclusively from plant sources, for example according to a method described in the document US 2008/0287722.

Alternatively, commercially available alkanes a) and b), for example the substances available under the trade names Parafol® 12-97 (INCI name: Dodecane) and Parafol® 22-95 (INCI name: Docosane), can also be used in the hair treatment agents as contemplated herein.

The linear alkanes a) and b) are preferably used in the hair treatment agents as contemplated herein with a percentage by weight of from about 0.1 to about 20 wt. % (more preferably from about 0.15 to about 17 wt. %, particularly preferably from about 0.2 to about 15 wt. %, and most preferably from about 0.25 to about 10 wt.) relative to the total weight of the hair treatment agents.

It is particularly preferred that from about 0.1 to about 20 wt. % dodecane and from about 0.1 to about 20 wt. % docosane are used in the hair treatment agents as contemplated herein.

As for the cosmetic effect, it has proven even more advantageous to use linear alkanes a) and b)—in particular dodecane and docosane—in a weight ratio a):b) of from about 10:90 to about 90:10, more preferably from about 20:80 to about 80:20, particularly preferably from about 30:70 to about 70:30, and most preferably from about 40:60 to about 60:40.

As a second essential constituent, the hair treatment agents as contemplated herein contain at least one amidoamine and/or a cationized amidoamine c).

Amidoamines and/or cationized amidoamines c) enhance the nourishing effect of hair treatment agents containing cationic nourishing agents and linear alkanes a) and b) by giving the hair more gloss, smoothness and softness and thus ensuring that hairbrushes or combs glide through the hair with as little resistance as possible.

Furthermore, amidoamines and/or cationized amidoamines c) contribute to an increase in the viscosity of the hair treatment agents, meaning that there is no need to use synthetic thickening agents such as acrylic acid (derivative) polymers.

Suitable amidoamines and/or cationized amidoamines c) as contemplated herein should be understood, for example, as compounds of the following formula (A-1)

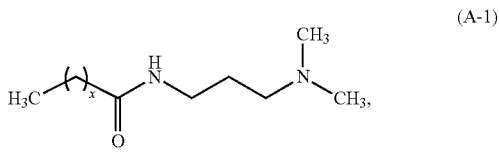

(A-1)

where
x denotes the number 18, 19, 20, 21, 22, 23 or 24.
Compounds of the formula (A-1) with x=20 are particularly preferred.

Preferred compounds according to formula (A-1) are commercially available under the INCI name Brassicamidopropyl Dimethylamine, for example under the trade names Kerabase® LC or ProCondition® 22 from Inolex Personal Care Ingredients.

Furthermore, suitable amidoamines and/or cationized amidoamines c) as contemplated herein can be selected from compounds of the following formula (A-2)

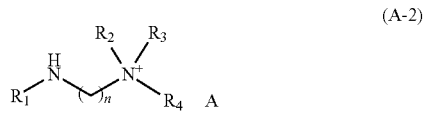

(A-2)

wherein
 $R_1$ denotes an acyl or alkyl radical with from about 6 to about 30 C atoms, which can be branched or unbranched, saturated or unsaturated, and wherein the acyl radical and/or the alkyl radical can contain at least one OH group,
 $R_2$, $R_3$ and $R_4$ each independently denote
 (i) hydrogen,
 (ii) an alkyl radical with from 1 to 4 C atoms, which can be the same or different, saturated or unsaturated, or
 (iii) a branched or unbranched hydroxyalkyl group with from 1 to 4 carbon atoms, which can be substituted with at least one, and at most three, hydroxy groups, for example —$CH_2OH$, —$CH_2CH_2OH$, —$CHOHCHOH$, —$CH_2CHOHCH_3$, —$CH(CH_2OH)_2$, —$COH(CH_2OH)_2$, —$CH_2CHOHCH_2OH$, —$CH_2CH_2CH_2OH$, and hydroxybutyl radicals, A denotes a physiologically compatible anion, and
n denotes an integer from 1 to 10.

Halogenide ions, sulfate ions, phosphate ions, methosulfate ions, as well as organic ions such as lactate-, citric-, tartrate- and acetate ions, for example, come into consideration as a physiologically compatible counterion A. Methosulfates and halogenide ions, more particularly chloride, are preferred.

A hair treatment agent is preferred, in which the amidoamine and/or the quaternized amidoamine according to the general formula (A-2) is an amidoamine and/or a quaternized amidoamine, wherein $R_1$ denotes a branched or unbranched, saturated or unsaturated acyl radical with from 6 to 30 C atoms, which can contain at least one OH group. Particular preference is given to a fatty acid radical of oils and waxes, in particular natural oils and waxes. Lanolin, beeswax and candelilla wax are examples of this.

Preference is also given to such amidoamines and/or quaternized amidoamines, in which $R_2$, $R_3$ and/or $R_4$ in the formula (A-2) denote a radical according to the general formula $CH_2CH_2OR_5$, wherein $R_5$ can denote alkyl radicals with from 1 to 4 carbon atoms, hydroxyethyl or hydrogen. It is preferred that n in the general formula (A-2) is an integer between from 2 and 5.

The alkylamidoamine c) according to formula (A-2) can be present as such and can also be transferred to the hair treatment agent by employing protonation in an accordingly acidic solution in a quaternary compound.

Cationic acylamidoamines according to formula (A-2) are preferred as contemplated herein.

As contemplated herein, examples of preferred amidoamines c) according to formula (A-2) are the compounds known under the INCI names Lauramidopropyl Dimethylamine (e.g. Mackine® 801), Lauramidopropyl Dimethylamine Propionate, Stearamidopropyl Dimethylamine (e.g. Adogen® S18V or Tego® Amid S 18 or Incromine® SB), Myristamidopropyl Dimethylamine (e.g. Schercodine® M), Stearamidoethyl Diethylamine (e.g. Lexamine® 22), Stearamidoethyl Diethylamine Phosphate, Cocamidopropyl Dimethylamine (e.g. Mackine® 101), Ricinolamidopropyl Dimethylamine (e.g. Mackine® 201), Isostearamidopropyl Dimethylamine (e.g. Mackine® 401), Oleamidopropyl Dimethylamine (e.g. Mackine® 501), Behenamidopropyl Dimethylamine (e.g. Mackine® 601, Incromine® BD), Cocamidopropyl Dimethylamine Propionate (e.g. Mackalene® 117), Cocamidopropyl Dimethylamine Lactate (e.g. Mackalene® 116), Ricinoleamidopropyl Dimethylamine Lactate (e.g. Mackalene® 216), Stearamidopropyl Dimethylamine Lactate (Mackalene® 316), Behenamidopropyl Dimethylamine Lactate (e.g. Mackalene® 616), Sunflowerseedamidopropyl Dimethylamine Lactate (e.g. Mackalene® 1216), Palmamidopropyl Dimethylamine, Palmamidopropyl Dimethylamine Lactate, Palmamidopropyl Dimethylamine Propionate, Oleamidopropyl Dimethylamine Glycolate, and Oleamidopropyl Dimethylamine Lactate.

Examples of permanent cationic amidoamines are the compounds known under the INCI names Quaternium-33 (e.g. Swamol®, Lanoquat® of DES-50), Behenamidopropyl Ethyldimonium Ethosulfate (e.g. Schercoquat® BAS), Behenamidopropyl PG-Dimonium Chloride (e.g. Lexquat® AMG-BEO), Oleamidopropyl Ethyldimonium Ethosulfate, Oleamidopropyl PG-Dimonium Chloride (e.g. Lexquat® AMG-O), Cocamidopropyl Ethyldimonium Ethosulfate (e.g. Schercoquat® CAS), Cocamidopropyltrimoniumchloride (e.g. Empigen® CSC), Ricinoleamidopropylethyldimonium Ethosulfate, Rinoleamidopropyltrimoniumchloride, Ricinoleamidopropyltrimoniummethosulfate (e.g. Rewoquat® RTM 50), Stearamidopropyl Ethyldimonium Ethosulfate (e.g. Schercoquat® SAS), Stearamidopropyl Trimonium Methosulfate (e.g. Catagene® SA-70), Undecyleneamidopropyltrimonium Methosulfate (e.g. Rewoquat® UTM 50), Lauramidopropyl PG-Dimonium Chloride, and Canolamidopropyl Ethyldimonium Ethosulfate (e.g. Schercoquat® COAS).

Preferred amidoamines and/or cationized amidoamines c) according to formula (A-2) are the compounds known under the INCI names Lauramidopropyl Dimethylamine, Myristamidopropyl Dimethylamine, Stearamidopropyl Dimethylamine, Cocamidopropyl Dimethylamine, Ricinolamidopropyl Dimethylamine, Isostearamidopropyl Dimethylamine, Oleamidopropyl Dimethylamine, Behenamidopropyl Dimethylamine, Palmamidopropyl Dimethylamine, Quaternium-33, Behenamidopropyl Ethyldimonium Ethosulfate, Oleamidopropyl Ethyldimonium Ethosulfate, Cocamidopropyltrimoniumchloride, Rinoleamidopropyltrimoniumchloride, Stearamidopropyl Trimonium Methosulfate, and mixtures thereof.

Particular preference is given to the amidoamines Stearamidopropyl Dimethylamine, Cocamidopropyl Dimethylamine, Ricinolamidopropyl Dimethylamine, Isostearamidopropyl Dimethylamine, Oleamidopropyl Dimethylamine, Behenamidopropyl Dimethylamine, Palmamidopropyl Dimethylamine, Quaternium-33, and Behenamidopropyl Ethyldimonium Ethosulfate.

Stearamidopropyl Dimethylamine, Cocamidopropyl Dimethylamine, Isostearamidopropyl Dimethylamine, Behenamidopropyl Dimethylamine, and Bis-Ethyl(isostearylimidazoline) Isostearamide are more particularly preferred. Stearamidopropyl Dimethylamine is most preferred.

In a third preferred embodiment, the hair treatment agents as contemplated herein contain at least one of the compounds known under the INCI names Brassicamidopropyl Dimethylamine, Stearamidopropyl Dimethylamine, Cocamidopropyl Dimethylamine, Behenamidopropyl Dimethylamine, Isostearamidopropyl Dimethylamine or Bis-Ethyl(isostearylimidazoline) Isostearamide as an amidoamine and/or cationized amidoamine c).

In this embodiment, particular preference is given to Brassicamidopropyl Dimethylamine and/or Stearamidopropyl Dimethylamine, most preferably Brassicamidopropyl Dimethylamine.

The aforementioned amidoamines and/or a cationized amidoamine c) can be used individually or in any combination, wherein they are contained in a total quantity of from about 0.1 to about 20.0 wt. %, more preferably in a total quantity of from about 0.15 to about 15.0 wt. %, particularly preferably in a total quantity of from about 0.2 to about 10 wt. %, and most preferably in a total quantity of from about 0.25 to about 5.0 wt. %, relative to the weight of the hair treatment agents as contemplated herein. The best results are obtained with a total quantity of from about 0.25 to about 5.0 wt. %, relative to the weight of the composition as contemplated herein.

As a third essential constituent, the hair treatment agents as contemplated herein contain at least one cationic surfactant d) differing from c), selected from esterquats (i) and/or quaternary ammonium compounds (ii).

The hair treatment agents as contemplated herein preferably contain at least one cationic surfactant d) in a total quantity from about 0.10 to about 20 wt. %, more preferably in quantities of from about 0.10 to about 10 wt. %, particularly preferably in quantities of from about 0.10 to about 7.5 wt. %, and most preferably in quantities of from about 0.10 to about 5.0 wt. %, relative to the total quantity of the agent.

This quantity is also not below or above this range if a mixture of these different compounds of quaternary ammonium compounds from group d) is used.

Consequently, the effectiveness of the hair treatment agent as contemplated herein is increased considerably beyond the additive effect to be expected, and the stability of the composition is significantly enhanced.

Suitable quaternary ammonium compounds (ii) can preferably be selected from compounds of the following formula (A-3)

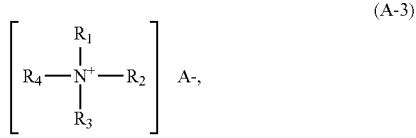

where

The radicals $R_1$, $R_2$, $R_3$ and $R_4$ each independently denote hydrogen, a methyl group, a phenyl group, a benzyl group or a saturated, branched or unbranched alkyl radical with a chain length of from 8 to 30 carbon atoms, which can be substituted with one or more hydroxy groups, with the proviso that at least one of the radicals $R_1$, $R_2$, $R_3$ and $R_4$ does not denote hydrogen, and A— denotes a physiologically compatible anion, for example a halogenide such as chloride or bromide, or methosulfate.

Examples of preferred compounds of the formula (A-3) are lauryl trimethyl ammonium chloride, cetyl trimethyl ammonium chloride, cetyl trimethyl ammonium bromide, cetyl trimethyl ammonium methosulfate, dicetyl dimethyl ammonium chloride, tricetyl methyl ammonium chloride, stearyl trimethyl ammonium chloride, distearyl dimethyl ammonium chloride, lauryl dimethyl benzyl ammonium chloride, behenyl trimethyl ammonium chloride, behenyl trimethyl ammonium bromide, and behenyl trimethyl ammonium methosulfate. Particularly preference is given to cetyl trimethyl ammonium chloride and/or behenyl trimethyl ammonium chloride.

Suitable esterquats (i) can preferably be selected from compounds of the following formula (A-4)

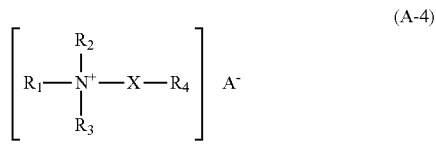

wherein the radicals $R_1$, $R_2$ and $R_3$, independently of each other, can be the same or different and denote the following:
- a branched or unbranched alkyl radical with from 1 to 4 carbon atoms, which can contain at least one hydroxyl group, or
- a saturated or unsaturated, branched or unbranched or a cyclic saturated or unsaturated alkyl radical with from 6 to 30 carbon atoms, which can contain at least one hydroxyl group, or
- an aryl or alkylaryl radical, such as phenyl or benzyl,
- the radical (—X—$R_4$), with the proviso that at most two of the radicals $R_1$, $R_2$ and $R_3$ can denote this radical, wherein X denotes:
- —$(CH_2)_n$— with n=from 1 to 20, preferably n=from 1 to 10, and particularly preferably n=from 1 to 5, or
- —$(CH_2—CHR_5—O)_n$— with n=from 1 to 200, preferably from 1 to 100, particularly preferably from 1 to 50, and most preferably from 1 to 20, and $R_5$ denotes hydrogen, or a methyl or ethyl group,
- a hydroxyalkyl group with one to four carbon atoms, which can be branched or unbranched, and which contains between one and three hydroxy groups. Examples are: —$CH_2OH$, —$CH_2CH_2OH$, —$CHOHCHOH$, —$CH_2CHOHCH_3$, —$CH(CH_2OH)_2$, —$COH(CH_2OH)_2$, —$CH_2CHOHCH_2OH$, —$CH_2CH_2CH_2OH$, and hydroxybutyl radicals, and $R_4$ denotes:
- the group $R_6$—O—CO—, wherein $R_6$ denotes a saturated or unsaturated, branched or unbranched or a cyclic saturated or unsaturated alkyl radical with from about 6 to about 30 carbon atoms, which can contain at least one hydroxy group, and which can also be oxyethylated with from 1 to 100 ethylene oxide units and/or from 1 to 100 propylene oxide units, or
- the group $R_7$—CO—, wherein $R_7$ denotes a saturated or unsaturated, branched or unbranched or a cyclic saturated or unsaturated alkyl radical with from about 6 to about 30 carbon atoms, which can contain at least one hydroxy group, and which can also be oxyethylated with from 1 to 100 ethylene oxide units and/or from 1 to 100 propylene oxide units, and $A^-$ denotes a physiologically compatible organic or inorganic anion, for example a halide ion such as chloride, bromide, iodide, a sulfation of the formula $RSO_3$—, wherein R denotes saturated or unsaturated alkyl radicals with from 1 to 4 carbon atoms, or an organic acidic anion such as maleate, fumarate, oxalate, tartrate, citrate, lactate or acetate.

Products according to formula (A-4) are sold, for example, under the trade names Rewoquat®, Stepantex®, Dehyquart®, Armocare® and Akypoquat®. The products Armocare® VGH-70, Dehyquart® F-75, Dehyquart® C-4046, Dehyquart® L80, Dehyquart® F-30, Dehyquart® AU-35, Rewoquat® WE18, Rewoquat® WE38 DPG, Stepantex® VS 90, and Akypoquat® 131 are examples of these esterquats (i).

Other suitable esterquats (i) as contemplated herein can be selected from compounds of the formula (A-5)

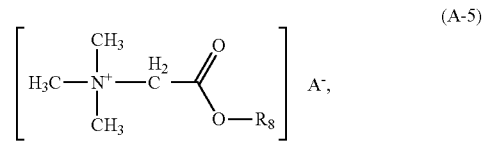

wherein the meaning of $R_8$ is in conformity with the meaning of $R_7$, and wherein $A^-$ has the same meaning as in formula (A-4).

The esterquats according to formula (A-5) with the trade names Armocare® VGH-70, and Dehyquart® F-75, Dehyquart® L80, Stepantex® VS 90 and Akypoquat® 131 are particularly preferred.

Most preferably, these esterquats are understood as those that are designated as Distearoylethyl Hydroxyethylmonium Methosulfate, Dicocoylethyl Hydroxyethylmonium Methosulfate, Dipalmitoylethyldimonium Chloride, and Behenoyl PG Trimonium Chloride according to the INCI nomenclature.

In a fourth preferred embodiment, the hair treatment agents as contemplated herein contain (relative to their weight)

from about 0.1 to about 20 wt. % of at least one linear alkane a),
from about 0.1 to about 20 wt. % of at least one linear alkane b),
from about 0.1 to about 20 wt. % of at least about one amidoamine and/or cationized amidoamine c), and
from about 0.1 to about 20 wt. % of at least one cationic surfactant d).

In this embodiment, it is most preferred if the hair treatment agents as contemplated herein (relative to their total weight) contains from about 0.1 to about 20 wt. % of at least one linear alkane a) known under the INCI name dodecane,
from about 0.1 to about 20 wt. % of at least one linear alkane a) known under the INCI name docosane,
from about 0.1 to about 20 wt. % of at least one amidoamine c) known under the INCI name brassicamidopropyl dimethylamine, and
from about 0.1 to about 20 wt. % of at least one esterquat (i) and/or a quaternary ammonium compound (ii), preferably at least one esterquat (i) and one quaternary ammonium compound (ii).

To further increase the hair-nourishing properties, it is also advantageous if the hair treatment agents as contemplated herein contain at least one other hair-nourishing ingredient.

The further hair nourishing agent can preferably be selected from ester oils e) with a percentage by weight of from about 0.1 to about 20 wt. % relative to the total weight of the hair treatment agent as contemplated herein, and/or
cationic polymers f) with a percentage by weight of from about 0.1 to about 10 wt. % relative to the total weight of the hair treatment agent as contemplated herein.

In a fifth preferred embodiment, the hair treatment agents as contemplated herein contain at least one ester oil e) with a percentage by weight of from about 0.1 to about 20 wt. % relative to the total weight of the hair treatment agent as contemplated herein.

In a sixth preferred embodiment, the hair treatment agents as contemplated herein contain at least one cationic polymer f) with a percentage by weight of from about 0.1 to about 10 wt. % relative to the total weight of the hair treatment agent as contemplated herein.

In a particularly preferred embodiment, the hair treatment agents as contemplated herein contain at least one ester oil e) and at least one cationic polymer f) in the aforementioned quantities.

Suitable ester oils e) as contemplated herein should be understood as esters of monobasic or multibasic $C_6$-$C_{30}$ fatty acids with monobasic or multibasic $C_2$-$C_{30}$ fatty alcohols. The mono esters of fatty acids with monovalent alcohols with from 2 to 24 C-atoms are preferred.

Examples of used fatty acid fractions in the esters are caproic acid, caprylic acid, 2-ethyl hexane acid, isononanoic acid, capric acid, lauric acid, isotridecaric acid, myristiric acid, palmitic acid, palmitoleic acid, stearic acid, isostearic acid, oleic acid, elaidic acid, petroselic acid, linolic acid, linolenic acid, elaeostearic acid, arachine acid, gadoleic acid, behen acid and eruca acid, as well as the technical mixtures thereof.

Examples of the fatty alcohol fractions in the ester oils are isopropylalcohol, glycerol, capronalcohol, aprylalcohol, 2-ethylhexylalcohol, nonyl alcohol, isononyl alcohol, caprinalcohol, laurylalcohol, isotridecylalcohol, myristylalcohol, cetylalcohol, palmoleylalcohol, stearylalcohol, isostearylalcohol, oleylalcohol, elaidylalcohol, petroselinylalcohol, linolylalcohol, linolenylalcohol, elaeostearylalcohol, arachylalcohol, gadoleylalcohol, behenylalcohol, erucylalcohol and brassidylalcohol, as well as technical mixtures thereof.

As contemplated herein, particular preference is given to isopropylmyristate, isononanoic acid C16-18 alkyl ester, 2-ethylhexyl palmitate, stearic acid 2-ethylhexyl ester, cetyl oleate, glycerol tricaprylate, coconut fatty alcohol caprinate/caprylate, n-butyl stearate, oleyl erucate, isopropyl palmitate, oleyl oleate, lauric acid hexyl ester, di-n-butyladipate, myristyl myristate, cetearyl isononanoate, isononyl isononanoate, oleic acid decyl ester, and mixtures thereof.

According to another particularly preferred embodiment, particular preferred ester oils e) are isopropylmyristate and/or isopropylpalmitate.

The ester oils e) can also optionally be alkoxylated with ethylene oxide, propylene oxide, or mixtures of ethylene oxide and propylene oxide. Alkoxylation can be carried out on the fatty alcohol part, on the fatty acid part or on both parts of the ester oils. However, as contemplated herein, it is preferred that the fatty alcohol is first alkoxylated and then esterified with fatty acid. These compounds are generally shown in the formula (E-1):

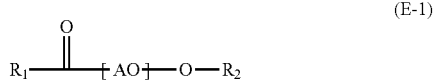

(E-1)

$R_1$ denotes a saturated or unsaturated, branched or unbranched, cyclically saturated or cyclically unsaturated acyl radical with from about 6 to about 30 carbon atoms, AO denotes ethylene oxide, propylene oxide or butylene oxide, X denotes a number between 1 and 200, preferably between 1 and 100, more preferably between 1 and 50, even more preferably between 1 and 20, particularly preferably between 1 and 10, and most preferably between 1 and 5, $R_2$ denotes a saturated or unsaturated, branched or unbranched, cyclically saturated or cyclically unsaturated alkyl, alkenyl, alkynyl, phenyl or benzyl radical with from 6 to 30 carbon atoms.

Examples of fatty acid fractions used as radical R1 in the esters are caproic acid, caprylic acid, 2-ethyl hexane acid, capric acid, lauric acid, isotridecaric acid, myristiric acid, palmitic acid, palmitoleic acid, stearic acid, isostearic acid, oleic acid, elaidic acid, petroselic acid, linolic acid, linolenic acid, elaeostearic acid, arachine acid, gadoleic acid, behen acid and eruca acid, as well as the technical mixtures thereof. Examples of the fatty alcohol fractions used as radical R2 in the ester oils are benzyl alcohol, isopropylalcohol, capronalcohol, aprylalcohol, 2-ethylhexylalcohol, caprinalcohol, laurylalcohol, isotridecylalcohol, myristylalcohol, cetylalcohol, palmoleylalcohol, stearylalcohol, isostearylalcohol, oleylalcohol, elaidylalcohol, petroselinylalcohol, linolylalcohol, linolenylalcohol, elaeostearylalcohol, arachylalcohol, gadoleylalcohol, behenylalcohol, erucylalcohol and brassidylalcohol, as well as technical mixtures thereof.

A preferred alkoxylated ester oil e) as contemplated herein is, for example, available under the INCI name PPG-3 Benzyl Ether Myristate.

Furthermore, ester oils e) should be understood as:
dicarbonic acid esters such as di-n-butyladipate, di-(2-ethylhexyl)-adipate, di-(2-ethylhexyl)-succinate and di-isotridecylacelaat, as well as diolesters such as ethylenglykol-dioleate, ethylenglykol-di-isotridecanoate, propylenglykol-di(2-ethylhexanoate), propylenglykol-di-isostearate, propylenglykol-di-pelargonate, butandiol-di-isostearate, neopentylglykoldicaprylate, and symmetric, asymmetric or cyclic esters of carbonic acid with fatty alcohols, for example glycerin carbonate or dicaprylyl carbonate (e.g. Cetiol® CC), Fatty acid partial glycerides, i.e. monoglycerides, diglycerides, and technical mixtures thereof. Typical examples are mono- and/or diglycerides based on caproic acid, caprylic acid, 2-ethyl hexane acid, capric acid, lauric acid, isotridecaric acid, myristiric acid, palmitic acid, palmoleic acid, stearic acid, isostearic acid, oleic acid, elaidic acid, petroselic acid, linolic acid, linolenic acid, elaeostearic acid, arachine acid, gadoleic acid, behen acid and eruca acid, as well as the technical mixtures thereof. Preferably, oleic acid monoglycerides are used.

natural oils. Examples of such oils are amaranthus seed oil, apricot kernel oil, arganil, avocado oil, babassu oil, cotton seed oil, borage oil, camel oil, safflower oil, peanut oil, grenadine core oil, grapefruit seed oil, hemp oil, hazelnut oil, hollowseed oil, currant seed oil, jojoba oil, coconut oil, linseed oil, macadamia nut oil, corn oil, almond oil, manila oil, evening primrose oil, olive oil, orange oil, palm oil, peach kernel oil, palm kernel oil, parannut oil, pectic oil, peach kernel oil, rapeseed oil, rice oil, sandalwood oil, sanddornkernel oil, sesame oil, soya oil, sunflower oil, grapeseed oil, walnut oil, wildtype oil, wheat germ oil, and the liquid fractions of coconut oil. However, other triglyceride oils, such as the liquid fractions of beef tallow and synthetic triglyceride oils, are also suitable.

Of course, as contemplated herein, it is also possible to use multiple ester oils e) simultaneously. Preferred ester oils are isopropylmyristate, glycerin carbonate, dicaprylyl carbonate, isopropyl palmitate, PPG-3 benzyl ether myristate, cetyl oleate, oceyl erucate, triglyceride (vegetable oils), and mixtures of at least two of these ester oils. Mixtures of ester oils, wherein one of the ester oils is isopropylpalmitate or isopropylmyristate, are particularly preferred. Mixtures of and with these two ester oils are most preferred.

In a further preferred embodiment, the at least one ester oil e) is contained in the agents as contemplated herein in a total quantity of from about 0.1 to about 10 wt. %, more preferably from about 0.1 to about 7.5 wt. %, particularly preferably from about 0.1 to about 6.0 wt. %, and most preferably from about 0.1 to about 5.0 wt. %, relative to the weight of the composition as contemplated herein.

As contemplated herein, suitable cationic polymers f) can preferably be selected from:
cationic polymers, which are derived from natural polymers, such as derivatives of polysaccharides, cationic derivatives of cellulose, starch or guar, for example. Cationic polysaccharides have the general formula G-O—B—N+$R_a R_b R_c$ A$^-$, wherein
G is an anhydroglucose radical, for example starch or cellulose anhydroglucose;
B is a divalent compound group, for example alkyles, oxyalkyles, polyoxyalkyles or hydroxyalkyles;
$R_a$, $R_b$ and $R_c$ are, independently of one another, alkyl, aryl, alkylaryl, arylalkyl, alkoxyalkyl or alkoxyaryl, each having up to 18 carbon atoms, wherein the total number of carbon atoms in $R_a$, $R_b$ and $R_c$ is preferably a maximum of 20;
A$^-$ is a common counter-ion, preferably chloride.

polymers derived from natural cationic polymers, such as hydrophobically modified cationic cellulose. Such cationic celluloses are commercially available with various degrees of substitution, cationic charge density, nitrogen content and molecular weights. In particular, the following modified cationic celluloses are most preferable as contemplated herein:

Polyquaternium-67; commercially available under the trade names Polymer® SL or Polymer® SK (Amerchol), for example.

Another highly preferred cellulose is offered under the trade name Mirustyle® CP from Croda. This is a cellulose derivatized as trimonium and cocodimonium hydroxyethylcellulose having the INCI trade name Polyquaternium-72. Polyquaternium-72 can be used both in solid form and also pre-dissolved in a hydrous solution.

Suitable cationic polymers, which are derived from synthetic polymers, are, for example, copolymers of
A1) from about 0.1 to about 50%, preferably from about 10 to about 50% (relative to the total number of monomers in the copolymer), monomers of the formula (Ia)

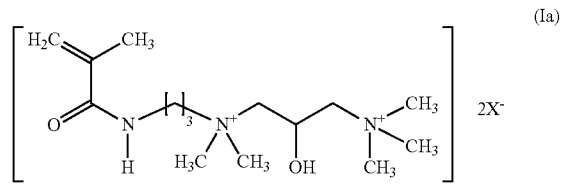

where
X denotes chloride, sulfate or methosulfate, and
A2) monomers from the group of acrylic acid, methacryl acid, as well as the alkali metal and ammonium salts of said acids,
wherein the monomer A2 makes up from about 50 to about 99.9%, preferably from about 50 to about 90% (relative to the total number of monomers in the copolymer), of the copolymer;

Regardless of which copolymers A are used in the agents as contemplated herein, preference is given to hair treatment agents as contemplated herein, wherein the copolymer A has a molar mass of from about 10,000 to about 20 million g/mol$^{-1}$, preferably from about 100,000 to about 10 million g/mol$^{-1}$, more preferably from about 500,000 to about 5 million g/mol$^{-1}$, and most preferably from about 1.1 million to about 2.2 million g/mol$^1$.

A most preferred polymer, constructed as illustrated above, is commercially available under the trade name Polyquaternium-74.

A further highly preferred cationic synthetic polymer is the optionally cross-linked homopolymer poly(methacryloyloxyethyl trimethyl ammonium chloride) with the INCI name Polyquaternium-37. Such products are commercially available under the trade names Rheocare® CTH (Cosmetic Rheologies) and Synthalen® CR (3V Sigma).

The homopolymer is preferably used in the form of an anhydrous polymer dispersion. Such polymer dispersions are commercially available under the trade names Salcare® SC 95 and Salcare® SC 96.

In a further preferred embodiment, the at least one cationic polymer f) is used in the hair treatment agents as contemplated herein in a quantity of from about 0.1 to about 5 wt. %, preferably from about 0.1 to about 2.5 wt. %, more preferably from about 0.1 to about 1 wt. %, particularly preferably from about 0.1 to about 0.75 wt. %, and most preferably from about 0.1 to about 0.5 wt. % (relative to the total weight of the hair treatment agent).

The hair treatment agents most preferably contain Polyquaternium-37 in the aforementioned quantities.

Additional positive effects of the hair treatment agents as contemplated herein can be achieved if plant extracts (L) are added to them.

As contemplated herein, extracts of green tea, oak bark, stinging nettle, witch hazel, hops, henna, chamomile, burdock root, horsetail, hawthorn, lime blossom, almond, aloe vera, spruce needle, horse chestnut, date palm, cinnamon tree, sandalwood, juniper, coconut, mango, apricot, lemon, wheat, kiwi, melon, orange, grapefruit, sage, rosemary, birch, mallow, valerian, cuckoo flower, creeping thyme, yarrow, thyme, balm, restharrow, coltsfoot, mallow, meristem, ginseng, coffee, cocoa, moringa, ginger root and ayurvedic plant extracts such as *Aegle marmelos* (bael), *Cyperus rotundus* (nagar motha), *Emblica officinalis* (Amalki), *Morinda citrifolia* (Ashyuka), *Tinospora cordifolia* (Guduchi), *Santalum album* (Chandana), *Crocus sativus* (kumkuma), *Cinnamonum zeylanicum* and *Nelumbo nucifera* (kamala), sweet grasses such as wheat, barley, rye, oats, spelt, maize, the various types of millet (proso millet, finger millet, foxtail millet, for example), sugar cane, ryegrass, meadow foxtail, oatgrass, bentgrass, meadow fescue, moor grass, bamboo, cotton grass, fountain grasses, Andropogonodeae (*Imperata cylindrica*, also known as cogon grass), buffalo grass, Spartina, Bermuda grass, lovegrasses, *Cymbopogon* (lemongrass), Oryzeae (rice), *Zizania* (wild rice), beachgrass, Helictotrichon, soft grasses, quaking grasses, meadow grasses, wild rye and *Echinacea*, in particular *Echinacea* angustifolia DC, *Echinacea paradoxa* (Norton), *Echinacea simulata*, *E. atrorubens*, *E. tennesiensis*, *Echinacea strigosa* (McGregor), *Echinacea laevigata*, *Echinacea purpurea* (L.) *Moench* and *Echinacea pallida* (Nutt), all types of wine, and pericarp of *Litchi chinensis* are most preferred.

Suitable extracts can be obtained from the fruits, seeds, flowers, roots, leaves and/or bark of the aforementioned plants.

As contemplated herein, the plant extracts can be used in both pure and diluted form. If they are used in diluted form, they usually contain approx. from about 2 to about 80 wt. % active substance and the extracting agent or mixture extracting agents used for their procurement as a solvent. Suitable extracting agents are usually water and/or alcohols.

In a preferred embodiment, the hair treatment agents as contemplated herein contain hydrous-alcoholic extracts of rice, the fruits of the date palm and/or the bark of the cinnamon tree.

The plant extract(s) can preferably be used in the hair treatment agents as contemplated herein in total quantities of from about 0.001 to about 1 wt. %, wherein the quantity specified is relative to the weight of the hair treatment agents.

Particularly good hair nourishing results (particular in regard to sensory characteristics such as softness, smoothness and combability) are achieved when the hair treatment agents as contemplated herein do not contain any further fatty constituents—in particular no silicons—in addition to the aforementioned linear alkanes a) and b) and optionally in addition to the ester oils e).

In a further preferred embodiment, the hair treatment agents as contemplated herein are therefore essentially free of silicons.

"Essentially free" means that the hair treatment agents as contemplated herein preferably contain less than about 0.1 wt. % silicon, more preferably less than about 0.05 wt. % silicon, and most preferably no silicons whatsoever (relative to the total weight of the hair treatment agents).

The aforementioned quantity specifications apply to both freely added silicon and silicons that can be contained as a by-product in commercial products.

A further synergistic active ingredient as contemplated herein in the compositions as contemplated herein with the active ingredient combination as contemplated herein is protein hydrolysates and/or derivatives thereof (P).

As contemplated herein, protein hydrolysates of plant, animal, marine or synthetic origin can be used.

Animal-based protein hydrolysates include elastin-, collagen-, Keratin-, silk- and milk protein hydrolysates, which can also exist in the form of salts.

Furthermore, as contemplated herein, preference is given to plant protein hydrolysates, such as soya, almond, pea, moringa, potato and wheat protein hydrolysates. Such products are available under the trade names Gluadin® (BASF), DiaMin® (Diamalt), Lexein® (Inolex), Hydrosoy (Croda), Hydrolupin (Croda), Hydrosesame (Croda), Hydrotritium® (Croda), Crotein® (Croda) and Puricare® LS 9658 from Laboratoires Sérobiologiques, for example.

Further preferred protein hydrolysates as contemplated herein are of maritime origin. This includes, for example, collagen hydrolysate from fish or algae, protein hydrolysates from mussels, and pearl hydrolysate. Examples of pearl extracts as contemplated herein are the commercial products Pearl Protein Extract BG® or Crodarom® Pearl.

The protein hydrolysates (P) can be contained in the hair treatment agents as contemplated herein (relative to their total weight) in quantities of from about 0.001 wt. % to about 20 wt. %, preferably from about of 0.05 wt. % to about 15 wt. %, and most preferably in quantities of from about 0.05 wt. % to about 5 wt. %.

The effect of the compositions as contemplated herein can also be enhanced by employing a 2-Pyrrolidinone-5-carboxylic acid and derivatives thereof (J). Preference is given to sodium, potassium, calcium, magnesium or ammonium salts, wherein the ammonium ion has one to three $C_1$- to $C_4$ alkyl groups in addition to hydrogen. Sodium salt is most preferred. The quantities used in the agents as contemplated herein amount to from about 0.05 to about 10 wt. %, relative to the total agent, more preferably from about 0.1 to about 5 wt. %, and most preferably from about 0.1 to about 3 wt. %.

A further preferred group of ingredients of the compositions as contemplated herein with the active ingredient combination as contemplated herein are vitamins, provitamins and vitamin precursors.

Particularly preference is given to vitamins, provitamins and vitamin precursors that are assigned to the groups A, B, C, E, F and H.

The group of substances called vitamin A includes retinol (vitamin $A_1$) and 3,4-didehydroretinol (vitamin $A_2$). β-carotin is the provitamin of retinal. As contemplated herein, vitamin A components can include vitamin A acid and the esters thereof, vitamin A aldehyde and vitamin A alcohol, as well as the esters thereof, such as palmitate and acetate. The agents as contemplated herein preferably contain the vitamin A component in quantities of from about 0.05 to about 1 wt. %, relative to the total preparation.

The vitamin B group or vitamin B complex includes:
Vitamin $B_1$ (Thiamin)
Vitamin $B_2$ (Riboflavin)
Vitamin $B_3$. The compounds nicotinic acid amide (niacin amide) are often carried under this designation. As contemplated herein, preference is given to nicotinic acid amide, which can be contained in the agents as contemplated herein preferably in quantities of from about 0.05 to about 1 wt. %, relative to the total agent.
Vitamin $B_5$ (pantothenic acid, panthenol and pantolacton). Among this group, panthenol and/or pantolacton is preferably used. Usable derivatives of panthenol as contemplated herein include, in particular, the esters and ethers of panthenol, as well as cationically derivatized panthenols. Specific examples are panthenoltriacetate, panthenolmonoethylether and the monoacetate thereof, as well as cationic panthenol derivatives. Pantothenic acid is preferably used as a derivative in the form of more stable calcium salt and sodium salt (Ca-pantothenate, Na-pantothenate) in the present disclosure.
Vitamin $B_6$ (pyridoxine, as well as pyridoxamine and pyridoxal).

The specified vitamin B-type compounds, in particular vitamin $B_3$, $B_5$ and $B_6$, can preferably be used in the agents as contemplated herein in quantities of from about 0.05 to about 10 wt. %, relative to the total agent. Quantities of from about 0.1 to about 5 wt. % are most preferred.

Vitamin C (ascorbic acid). Vitamin C can preferably be used in the agents as contemplated herein in quantities of from about 0.1 to about 3 wt. %, relative to the total agent. Use in the form of palmitic acid ester, glucoside or phosphate can be preferred. Use in combination with tocopherolene can also be preferred.

Vitamin E (tocopheroles, more particularly α-tocopherole). Tocopherole and its derivatives, which in particular includes esters such as acetate, nicotinate, phosphate and succinate, can preferably be used in the agents as contemplated herein in quantities of from about 0.05 to about 1 wt. %, relative to the total agent.

Vitamin F. The term "vitamin F" usually means essential fatty acids, more particularly linoleic acid, linolenic acid and arachidon acid.

Vitamin H. The compound (3aS,4S,6aR)-2-oxohexahydrothienol[3,4-d]-imidazol-4-valeric acid, which has however since taken on the trivial name of biotin, is designated as vitamin H. Biotin can preferably be contained in the agents as contemplated herein in quantities of from about 0.0001 to about 1.0 wt. %, more preferably in quantities of from about 0.001 to about 0.01 wt. %.

The compositions as contemplated herein preferably contain vitamins, provitamins and vitamin precursors from the groups A, B, E and H. Particular preference is given to panthenol, pantolacton, pyridoxine and its derivatives, as well as nicotinic acid amide and biotin.

The following betaines are a further preferred group of ingredients in the cosmetic compositions as contemplated herein: carnitine, carnitine tartrate, carnitine magnesium citrate, acetylcamitin, betalains, 1.1-dimethyl-proline, choline, cholin chloride, cholin bitartrate, cholin dihydrogen citrate and the compound N,N,N-trimethylglycine, which is referred to in the literature as betaine.

Carnitine, histidine, choline and betaine are preferably used. In a particularly preferred embodiment of the present disclosure, L-carnitine tartrate is used as an active ingredient.

A further ingredient is taurine and/or a derivative thereof. Taurine should exclusively be understood as 2-aminoethanesulfonic acid, and a derivative should be understood as the explicitly specified derivatives of taurine. Derivatives of taurine should be understood as N-monomethyl taurine, N,N-dimethyl taurine, taurine lysylate, taurine tartrate, taurine omithate, lysyl taurine, and omithyl taurine. In the context of the present disclosure, further taurine derivatives are taurocholic acid and hypotaurine.

Agents as contemplated herein can contain one or more of the aforementioned active ingredients, preferably in quantities of from about 0.0001 to about 10.0 wt. %, more preferably from about 0.0005 to about 5.0 wt. %, particularly preferably of from about 0.001 to about 2.0 wt. %, and most preferably from about 0.001 to about 1.0 wt. % (relative to the total weight of the agent). Particular preference is given to taurine and/or a derivative thereof.

The agents as contemplated herein can also contain at least one UV light protection filter. These can be oil-soluble or water-soluble.

Oil-soluble substances include, for example:
3-benzylidene camphor, e.g. 3-(4-methylbenzylidene)camphor;
4-aminobenzoic acid derivatives, preferably 4-(dimethylamino)benzoic acid-2-ethylhexyl ester, 4-(dimethylamino)benzoic acid-2-octyl ester, and 4-(dimethylamino) benzoic acid amyl ester;
esters of cinnamic acid, preferably 4-methoxy cinnamic acid-2-ethylhexyl ester, 4-methoxy cinnamic acid propyl ester, 4-methoxy cinnamic acid isoamyl ester, and 2-cyano-3-phenyl-cinnamic acid-2-ethylhexyl ester (octocrylene);
esters of salicylic acid, preferably salicylic acid-2-ethylhexyl ester, salicylic acid-4-isopropylbenzyl ester, and salicylic acid homomenthyl ester;
derivatives of benzophenones, preferably 2-hydroxy-4-methoxybenzophenone, 2-hydroxy-4-meth-oxy-4'-methylbenzophenone, and 2.2'-dihydroxy-4-methoxybenzophenone;
esters of benzalmalonic acid, preferably 4-methoxy benzalmalonic acid di-2-ethylhexyl ester;
triazine derivatives, such as 2,4,6-trianilino-(p-carbo-2'-ethylhexyl-1'-oxy)-1,3,5-triazine and octyl triazone.
propane-1,3-diones, such as 1-(4-tert.butylphenyl)-3-(4'methoxyphenyl)propane-1,3-dione;

Water-soluble substances include:
2-phenylbenzimidazol-5-sulfonic acid and its alkali-, alkaline earth-, ammonium-, alkylammonium-, alkanolammonium- or glucammonium salts;
sulfonic acid derivatives of benzophenones, preferably 2-hydroxy-4-methoxybenzophenone-5-sulfonic acid, and salts thereof
sulfonic acid derivatives of 3-benzylidene camphor, such as 4-(2-oxo-3-bornylidenmethyl)benzol sulfonic acid and 2-methyl-5-(2-oxo-3-bornylide)sulfonic acid, and salts thereof.

Typical UV-A filters include, in particular, derivatives of benzoyl methane, such as 1-(4'-tert.butylphenyl)-3-(4'-methoxyphenyl)propane-1,3-dione or 1-phenyl-3-(4'-isopropylphenyl)-propane-1,3-dione.

Of course, the UV-A and UV-B filters can also be used in mixtures. In addition to the specified soluble substances, non-soluble pigments are also considered for this purpose, in particular finely dispersed metal oxides and salts, such as titanium dioxide, zinc oxide, iron oxide, aluminum oxide, cerium oxide, zirconium oxide, silicate (talc), barium sulfate, and zinc stearate. The particles should have an average diameter of less than about 100 nm, preferably between from about 5 and about 50 nm, and most preferably between from about 15 and about 30 nm. They can have a spherical form, although particles having an ellipsoidal shape or differing in any other way from the spherical form can also be used.

Furthermore, the hair treatment agents as contemplated herein can contain further active ingredients, auxiliary ingredient and additives, for example acidifying agents such as citric acid and lactic acid, dimethyl isosorbide and cyclodextrins, dyes to color the agent, anti-dandruff active ingredients such as piroctone olamine, zinc omadine and climbazol, complexing agents such as EDTA, NTA, β-alanine diacetic acid and phosphonic acids, opacifiers such as latex, styrene/PVP and styrene/acrylamide copolymers; pearl shine concentrates such as ethylenglycolmono- and -distearate as well as PEG-3-distearate; pigments, stabilizing agents for hydrogen peroxide and other oxidants, propellants such as propane-butane mixtures, $N_2O$, dimethyl ether, $CO_2$ and air, antioxidants, perfume oils, fragrances and scents.

With regard to further optional components and the amounts of these components used, reference is expressly made to the relevant handbooks known to the person skilled in the art.

Furthermore, for an optimal product performance, it is advantageous if the hair treatment agents as contemplated herein have a pH value in the range of from about 2.5 to about 4.5, more preferably from about 3.0 to about 4.5, and in particular from about 3.0 to about 4.0.

A second subject of the present disclosure is a cosmetic method to nourish hair, wherein a hair treatment agent as contemplated herein is applied to the hair and is rinsed out with water after an exposure time from a few seconds to about 45 minutes.

A third subject of the present disclosure is the cosmetic use of the hair treatment agent as contemplated herein to nourish hair, in particular to improve
the wet and dry combability,
the disentanglement,
the gloss, and
the hold of hair.

With respect to other preferred embodiments of the use as contemplated herein and of the method as contemplated herein, the statements made regarding the agents as contemplated herein apply mutatis mutandis.

The following examples are intended to explain the subject matter of the present disclosure without, however, having any limiting effect.

Examples

All quantities are specified in wt-%. The following hair treatment agents as contemplated herein were prepared using known production methods:

| | 1 | 2 | 3 | 4 |
|---|---|---|---|---|
| Amidoamine and/or cationized amidoamine | 0.10-20.00 | 0.15-15.00 | 0.20-10.00 | 0.25-5.00 |
| Esterquat and/or quaternary ammonium compound | 0.10-20.00 | 0.10-10.00 | 0.10-7.50 | 0.10-5.00 |
| Linear $C_9$-, $C_{10}$-, $C_{11}$- and/or $C_{12}$ alkane | 0.10-20.00 | 0.15-17.00 | 0.20-15.00 | 0.25-10.00 |
| Linear $C_{15}$-, $C_{16}$-, $C_{17}$-, $C_{18}$-, $C_{19}$-, $C_{20}$-, $C_{21}$-, $C_{22}$- and/or $C_{23}$ alkane | 0.10-20.00 | 0.15-17.00 | 0.20-15.00 | 0.25-10.00 |
| Water and other adjuvants and additives, where applicable | ad 100 | ad 100 | ad 100 | ad 100 |

| | 5 | 6 | 7 | 8 |
|---|---|---|---|---|
| Brassicamidopropyl Dimethylamine, Stearamidopropyl Dimethylamine, Cocamidopropyl Dimethylamine, Behenamidopropyl Dimethylamine, Isostearamidopropyl Dimethylamine and Bis-Ethyl(isostearylimidazoline) Isostearamide | 0.10-20.00 | 0.15-15.00 | 0.20-10.00 | 0.25-5.00 |
| Esterquat and/or quaternary ammonium compound | 0.10-20.00 | 0.10-10.00 | 0.10-7.50 | 0.10-5.00 |
| Linear $C_9$-, $C_{10}$-, $C_{11}$- and/or $C_{12}$ alkane | 0.10-20.00 | 0.15-17.00 | 0.20-15.00 | 0.25-10.00 |
| Linear $C_{15}$-, $C_{16}$-, $C_{17}$-, $C_{18}$-, $C_{19}$-, $C_{20}$-, $C_{21}$-, $C_{22}$- and/or $C_{23}$ alkane | 0.10-20.00 | 0.15-17.00 | 0.20-15.00 | 0.25-10.00 |
| Water and other adjuvants and additives, where applicable | ad 100 | ad 100 | ad 100 | ad 100 |

| | 9 | 10 | 11 | 12 |
|---|---|---|---|---|
| Brassicamidopropyl dimethylamine and/or stearamidopropyl dimethylamine | 0.10-20.00 | 0.15-15.00 | 0.20-10.00 | 0.25-5.00 |
| Esterquat and/or quaternary ammonium compound | 0.10-20.00 | 0.10-10.00 | 0.10-7.50 | 0.10-5.00 |
| Linear $C_9$-, $C_{10}$-, $C_{11}$- and/or $C_{12}$ alkane | 0.10-20.00 | 0.15-17.00 | 0.20-15.00 | 0.25-10.00 |

-continued

| | | | | |
|---|---|---|---|---|
| Linear $C_{15}$-, $C_{16}$-, $C_{17}$-, $C_{18}$-, $C_{19}$-, $C_{20}$-, $C_{21}$-, $C_{22}$- and/or $C_{23}$ alkane | 0.10-20.00 | 0.15-17.00 | 0.20-15.00 | 0.25-10.00 |
| Water and other adjuvants and additives, where applicable | ad 100 | ad 100 | ad 100 | ad 100 |

| | 13 | 14 | 15 | 16 |
|---|---|---|---|---|
| Amidoamine and/or cationized amidoamine | 0.10-20.00 | 0.15-15.00 | 0.20-10.00 | 0.25-5.00 |
| Esterquat and/or quarternary ammonium compound | 0.10-20.00 | 0.10-10.00 | 0.10-7.50 | 0.10-5.00 |
| Dodecane | 0.10-20.00 | 0.15-17.00 | 0.20-15.00 | 0.25-10.00 |
| Linear $C_{15}$-, $C_{16}$-, $C_{17}$-, $C_{18}$-, $C_{19}$-, $C_{20}$-, $C_{21}$-, $C_{22}$- and/or $C_{23}$ alkane | 0.10-20.00 | 0.15-17.00 | 0.20-15.00 | 0.25-10.00 |
| Water and other adjuvants and additives, where applicable | ad 100 | ad 100 | ad 100 | ad 100 |

| | 17 | 18 | 19 | 20 |
|---|---|---|---|---|
| Amidoamine and/or cationized amidoamine | 0.10-20.00 | 0.15-15.00 | 0.20-10.00 | 0.25-5.00 |
| Esterquat and/or quarternary ammonium compound | 0.10-20.00 | 0.10-10.00 | 0.10-7.50 | 0.10-5.00 |
| Dodecane | 0.10-20.00 | 0.15-17.00 | 0.20-15.00 | 0.25-10.00 |
| Docosane | 0.10-20.00 | 0.15-17.00 | 0.20-15.00 | 0.25-10.00 |
| Water and other adjuvants and additives, where applicable | ad 100 | ad 100 | ad 100 | ad 100 |

| | 21 | 22 | 23 | 24 |
|---|---|---|---|---|
| Amidoamine and/or cationized amidoamine | 0.10-20.00 | 0.15-15.00 | 0.20-10.00 | 0.25-5.00 |
| Esterquat and/or quarternary ammonium compound | 0.10-20.00 | 0.10-10.00 | 0.10-7.50 | 0.10-5.00 |
| Linear $C_9$-, $C_{10}$-, $C_{11}$- and/or $C_{12}$ alkane | 0.10-20.00 | 0.15-17.00 | 0.20-15.00 | 0.25-10.00 |
| Linear $C_{15}$-, $C_{16}$-, $C_{17}$-, $C_{18}$-, $C_{19}$-, $C_{20}$-, $C_{21}$-, $C_{22}$- and/or $C_{23}$ alkane | 0.10-20.00 | 0.15-17.00 | 0.20-15.00 | 0.25-10.00 |
| Ester oil | 0.10-20.00 | 0.10-10.00 | 0.10-7.50 | 0.10-5.00 |
| Water and other adjuvants and additives, where applicable | ad 100 | ad 100 | ad 100 | ad 100 |

| | 25 | 26 | 27 | 28 |
|---|---|---|---|---|
| Amidoamine and/or cationized amidoamine | 0.10-20.00 | 0.15-15.00 | 0.20-10.00 | 0.25-5.00 |
| Esterquat and/or quarternary ammonium compound | 0.10-20.00 | 0.10-10.00 | 0.10-7.50 | 0.10-5.00 |
| Linear $C_9$-, $C_{10}$-, $C_{11}$- and/or $C_{12}$ alkane | 0.10-20.00 | 0.15-17.00 | 0.20-15.00 | 0.25-10.00 |
| Linear $C_{15}$-, $C_{16}$-, $C_{17}$-, $C_{18}$-, $C_{19}$-, $C_{20}$-, $C_{21}$-, $C_{22}$- and/or $C_{23}$ alkane | 0.10-20.00 | 0.15-17.00 | 0.20-15.00 | 0.25-10.00 |
| Cationic polymer | 0.10-10.00 | 0.10-5.00 | 0.10-2.50 | 0.10-1.00 |
| Water and other adjuvants and additives, where applicable | ad 100 | ad 100 | ad 100 | ad 100 |

| | 29 | 30 | 31 | 32 |
|---|---|---|---|---|
| Amidoamine and/or cationized amidoamine | 0.10-20.00 | 0.15-15.00 | 0.20-10.00 | 0.25-5.00 |
| Esterquat and/or quarternary ammonium compound | 0.10-20.00 | 0.10-10.00 | 0.10-7.50 | 0.10-5.00 |
| Linear $C_9$-, $C_{10}$-, $C_{11}$- and/or $C_{12}$ alkane | 0.10-20.00 | 0.15-17.00 | 0.20-15.00 | 0.25-10.00 |
| Linear $C_{15}$-, $C_{16}$-, $C_{17}$-, $C_{18}$-, $C_{19}$-, $C_{20}$-, $C_{21}$-, $C_{22}$- and/or $C_{23}$ alkane | 0.10-20.00 | 0.15-17.00 | 0.20-15.00 | 0.25-10.00 |

|  | 33 | 34 | 35 | 36 |
|---|---|---|---|---|
| Ester oil | 0.10-20.00 | 0.10-10.00 | 0.10-7.50 | 0.10-5.00 |
| Cationic polymer | 0.10-10.00 | 0.10-5.00 | 0.10-2.50 | 0.10-1.00 |
| Water and other adjuvants and additives, where applicable | ad 100 | ad 100 | ad 100 | ad 100 |

|  | 33 | 34 | 35 | 36 |
|---|---|---|---|---|
| Brassicamidopropyl dimethylamine and/or stearamidopropyl dimethylamine | 3.00-30.00 | 4.00-25.00 | 4.50-20.00 | 5.00-15.00 |
| Esterquat and/or quarternary ammonium compound | 1.00-20.00 | 1.25-17.50 | 1.50-15.00 | 2.00-10.00 |
| Dodecane | 0.10-20.00 | 0.15-17.00 | 0.20-15.00 | 0.25-10.00 |
| Docosane | 0.10-20.00 | 0.15-17.00 | 0.20-15.00 | 0.25-10.00 |
| Ester oil | 0.10-20.00 | 0.10-10.00 | 0.10-7.50 | 0.10-5.00 |
| Cationic polymer | 0.10-10.00 | 0.10-5.00 | 0.10-2.50 | 0.10-1.00 |
| Water and other adjuvants and additives, where applicable | ad 100 | ad 100 | ad 100 | ad 100 |

|  | 37 | 38 | 39 | 40 |
|---|---|---|---|---|
| Brassicamidopropyl dimethylamine and/or stearamidopropyl dimethylamine | 3.00-30.00 | 4.00-25.00 | 4.50-20.00 | 5.00-15.00 |
| Esterquat and/or quarternary ammonium compound | 1.00-20.00 | 1.25-17.50 | 1.50-15.00 | 2.00-10.00 |
| Dodecane | 0.10-20.00 | 0.15-17.00 | 0.20-15.00 | 0.25-10.00 |
| Docosane | 0.10-20.00 | 0.15-17.00 | 0.20-15.00 | 0.25-10.00 |
| Isopropyl myristate | 0.10-20.00 | 0.10-10.00 | 0.10-7.50 | 0.10-5.00 |
| Guar hydroxypropyltrimonium chloride | 0.10-10.00 | 0.10-5.00 | 0.10-2.50 | 0.10-1.00 |
| Water and other adjuvants and additives, where applicable | ad 100 | ad 100 | ad 100 | ad 100 |

|  | 41 | 42 |
|---|---|---|
| Cetearyl alcohol | 4.0 | 4.0 |
| Isopropyl myristate | 1.0 | 1.0 |
| Parafol ®[1] 22-95 | 3.0 | 3.0 |
| Parafol ®[2] 12-97 | 3.0 | 3.0 |
| Dehyquart ®[3] F 75 T | 1.5 | 1.5 |
| Guar hydroxypropyltrimonium chloride | 0.1 | 0.1 |
| Behentrimonium chloride | 2.0 | 1.0 |
| Quartamine ®[4] BTC-131 | 2.0 | 2.0 |
| ProCondition ®[5] 22 |  | 2.0 |
| Stearamidopropyl dimethylamine | 2.0 |  |
| Glyceryl monostearate | 1.0 | 1.0 |
| Citric acid | 0.1 | 0.1 |
| Panthenol | 0.2 | 0.2 |
| Nicotinic acid amide | 0.2 | 0.2 |
| Gluadin ®[6] Soy | 0.5 | 0.5 |
| Crodarom Violet Rice ®[7] | 0.5 | 0.5 |
| Delice Extreme ®[8] | 0.5 | 0.5 |
| Phenoxyethanol | 0.5 | 0.5 |
| Perfume | 0.6 | 0.6 |
| Water | ad 100 | ad 100 |
| pH value | 3.0-4.0 | 3.0-4.0 |

List of raw materials used:
[1] INCI name: n-Dodecane; Sasol
[2] INCI name: n-Docosane; Sasol
[3] INCI name: Distearoylethyl Hydroxyethylmonium Methosulfate, Cetearyl Alcohol; cationic surfactant (AS) 65-72%, BASF
[4] INCI name: Behenoyl PG-Trimonium Chloride; Kao Chemicals
[5] INCI name: Brassicamidopropyl Dimethylamine; Inolex Personal Care Ingredients
[6] INCI name: Hydrolyzed Soy Protein; BASF
[7] INCI name: Aqua (Water), Glycerin, *Oryza Sativa* (Rice) Extract; Croda
[8] INCI name: Aqua (Water), Glycerin, *Phoenix Dactylifera* (Date) Fruit Extract, *Cinnamomum Zeylanicum* Bark Extract; Croda The compositions as contemplated herein are excellent hair care products and give hair improved combability, improved haptics and more gloss.

A slight improvement in nourishing properties was achieved in comparison with products containing silicons.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodi-

The invention claimed is:

1. A hair treatment agent, consisting essentially of:
    a) at least one linear alkane selected from $C_9$-, $C_{10}$-, $C_{11}$- and $C_{12}$ alkanes and mixtures of these alkanes; as long as the linear alkane comprises at least about 50 wt. % $C_{12}$ alkane (dodecane),
    b) at least one linear alkane selected from $C_{15}$-, $C_{16}$-, $C_{17}$-, $C_{18}$-, $C_{19}$-, $C_{20}$-, $C_{21}$-, $C_{22}$- and $C_{23}$ alkanes and mixtures of these alkanes; as long as the linear alkane b) comprises at least about 50 wt. % $C_{22}$ alkane (docosane),
    c) at least one amidoamine and/or a cationized amidoamine, and
    d) at least one cationic surfactant selected from
        i. esterquats and/or
        ii. quaternary ammonium compounds; and
    e) water.

2. The hair treatment agent according to claim 1, comprising relative to the weight of the hair treatment agent, from about 0.1 to about 20 wt. % of the at least one linear alkane a), from about 0.1 to about 20 wt. % of the at least one linear alkane b), from about 0.1 to about 20 wt. % of the at least one amidoamine and/or the cationized amidoamine c), and from about 0.1 to about 20 wt. % of the at least one cationic surfactant d).

3. The hair treatment agent according to claim 1, wherein the at least one linear alkane a) has an International Nomenclature Cosmetic Ingredient (INCI) name dodecane.

4. The hair treatment agent according to claim 1, wherein the at least one linear alkane has an INCI name docosane.

5. The hair treatment agent according to claim 1, wherein the amidoamine and/or cationized amidoamine c) has an INCI name of brassicamidopropyl dimethylamine, stearamidopropyl dimethylamine, cocamidopropyl dimethylamine, behenamidopropyl dimethylamine, isostearamidopropyl dimethylamine or bis-ethyl(isostearylimidazoline) isostearamide).

6. The hair treatment agent according to claim 5, wherein the amidoamine and/or cationized amidoamine c) has an INCI name brassicamidopropyl dimethylamine.

7. The hair treatment agents according to claim 1, further comprising at least one ester oil e) with a percentage by weight of from about 0.1 to about 20 wt. % relative to the total weight of the hair treatment agent.

8. The hair treatment agents according to claim 1, further comprising at least one cationic polymer f) with a percentage by weight of from about 0.1 to about 10 wt. % relative to the total weight of the hair treatment agent.

9. The hair treatment agent according to claim 6, further comprising at least one ester oil e) and at least one cationic polymer f).

10. The hair treatment agent according to claim 1, wherein the hair treatment agent is essentially free of silicones.

11. The hair treatment agent according to claim 1, wherein the hair treatment agent has a pH value in the range of from about 2.5 to about 4.5.

12. A method to nourish hair, comprising applying a hair treatment agent consisting of
    a) at least one linear alkane selected from $C_9$-, $C_{10}$-, $C_{11}$- and $C_{12}$ alkanes and mixtures of these alkanes; as long as the linear alkane comprises at least about 50 wt. % C12 alkane (dodecane),
    b) at least one linear alkane selected from $C_{15}$-, $C_{16}$-, $C_{17}$-, $C_{18}$-, $C_{19}$-, $C_{20}$-, $C_{21}$-, $C_{22}$- and $C_{23}$ alkanes and mixtures of these alkanes; as long as the linear alkane b) comprises at least about 50 wt. % C22 alkane (docosane),
    c) at least one amidoamine and/or a cationized amidoamine, and
    d) at least one cationic surfactant selected from
        i. esterquats and/or
        ii. quaternary ammonium compounds; and
    e) water
    to the hair, and rinsing out with water after an exposure time from about 2 seconds to about 45 minutes.

13. A method of hair management comprising applying a composition according to claim 1 to a persons hair for improving
    a wet and dry combability,
    a disentanglement,
    a gloss, and/or
    a hold of the hair.

* * * * *